(12) United States Patent
Shreve et al.

(10) Patent No.: US 9,618,486 B2
(45) Date of Patent: Apr. 11, 2017

(54) LIMITING A RATE OF PRESSURIZATION IN A PRESSURIZED FLOW SYSTEM HAVING A CONFIGURABLE SYSTEM VOLUME

(71) Applicant: Waters Technologies Corporation, Milford, MA (US)

(72) Inventors: Joshua A. Shreve, Franklin, MA (US); Paul Keenan, Harrisville, RI (US)

(73) Assignee: Waters Technologies Corporation, Milford, MA (US)

(*) Notice: Subject to any disclaimer, the term of this patent is extended or adjusted under 35 U.S.C. 154(b) by 124 days.

(21) Appl. No.: 14/381,977

(22) PCT Filed: Mar. 7, 2013

(86) PCT No.: PCT/US2013/029536
§ 371 (c)(1),
(2) Date: Aug. 28, 2014

(87) PCT Pub. No.: WO2013/134475
PCT Pub. Date: Sep. 12, 2013

(65) Prior Publication Data
US 2015/0034168 A1    Feb. 5, 2015

Related U.S. Application Data

(60) Provisional application No. 61/607,913, filed on Mar. 7, 2012.

(51) Int. Cl.
*G01N 30/32* (2006.01)
*B01D 15/16* (2006.01)
(Continued)

(52) U.S. Cl.
CPC .......... *G01N 30/32* (2013.01); *B01D 15/163* (2013.01); *G05D 7/0617* (2013.01);
(Continued)

(58) Field of Classification Search
CPC ................. B01D 15/163; B01D 15/40; G01N 2030/326; G01N 2030/328; G01N 30/32;
(Continued)

(56) References Cited

U.S. PATENT DOCUMENTS 4,984,602 A    1/1991   Saito et al.
5,114,314 A  * 5/1992   Fujimoto ............ F04B 11/0058
                                                                417/18
(Continued)

OTHER PUBLICATIONS

Guiochon G, et al., Fundamental challenges and opportunities for preparative supercritical fluid chromatography. J Chromatogr A. Feb. 25, 2011;1218(8):1037-114.
(Continued)

*Primary Examiner* — William McCalister
(74) *Attorney, Agent, or Firm* — McCarter & English, LLP; Deborah M. Vernon; Heath T. Misley (57) ABSTRACT

Exemplary embodiments of the present disclosure are directed to limiting a rate or pressurization in a reconfigurable pressurized flow system for which different system configurations can have different system volumes. In exemplary embodiments, the system can determine a limit for the rate of pressurization by configuring the system for a closed system rate of pressurization, measuring the closed system rate of pressurization at a set flow rate, and determining a relationship between the closed system rate of pressurization and the flow rate. The system can use the relationship to dynamically set the limit for different flow rates in the system.

7 Claims, 8 Drawing Sheets

(51) Int. Cl.
*G05D 16/20* (2006.01)
*G05D 7/06* (2006.01)
*B01D 15/40* (2006.01)

(52) U.S. Cl.
CPC ......... *G05D 16/2013* (2013.01); *B01D 15/40* (2013.01); *G01N 2030/326* (2013.01); *G01N 2030/328* (2013.01); *Y10T 137/0396* (2015.04); *Y10T 137/86002* (2015.04)

(58) Field of Classification Search
CPC .............. G05D 16/2013; G05D 7/0617; Y10T 137/0396; Y10T 137/86002
See application file for complete search history.

(56) References Cited

U.S. PATENT DOCUMENTS

| | | |
|---|---|---|
| 5,163,979 A | 11/1992 | Patrick et al. |
| 5,322,672 A | 6/1994 | Breuer et al. |
| 5,531,959 A * | 7/1996 | Johnson .................. G01N 30/00 210/198.2 |
| 5,711,786 A | 1/1998 | Hinshaw |
| 6,357,277 B1 * | 3/2002 | Pigozzo ............. G01N 30/8668 73/1.06 |
| 7,881,886 B1 * | 2/2011 | Shareef .................... G01F 1/36 137/10 |
| 8,561,627 B1 * | 10/2013 | Kelekar ............ H01L 21/67017 137/12 |
| 2004/0112435 A1 * | 6/2004 | Olander ............... G05D 7/0652 137/487.5 |
| 2010/0040483 A1 | 2/2010 | Berger et al. |
| 2011/0016951 A1 | 1/2011 | Reuter |
| 2012/0168142 A1 * | 7/2012 | Hernandez ........... E21B 36/001 165/279 |
| 2014/0260294 A1 * | 9/2014 | Farshchian ............... F23N 5/00 60/773 |
| 2015/0034168 A1 * | 2/2015 | Shreve .................. G01N 30/32 137/14 |
| 2015/0112493 A1 * | 4/2015 | Haggerty ................. G01F 3/38 700/282 |

OTHER PUBLICATIONS

International Search Report for PCT/US2013/029536, date mailed May 10, 2013.

* cited by examiner

LIMITING A RATE OF PRESSURIZATION IN A PRESSURIZED FLOW SYSTEM HAVING A CONFIGURABLE SYSTEM VOLUME

RELATED APPLICATION

This application is a National Stage Application of International Application No. PCT/US2013/029536, filed Mar. 7, 2013, which claims priority to U.S. Provisional Application No. 61/607,913, filing date Mar. 7, 2012. Each of the foregoing applications is incorporated herein by reference in its entirety.

FIELD OF THE TECHNOLOGY

In general, the field of the technology of the present disclosure is directed to methods, processes, systems and computer readable instructions for controlling pressurization in a pressurized flow system, such as, for example, a $CO_2$-based chromatography or a $CO_2$-based extraction system. In particular, the technology of the present disclosure is directed to controlling (e.g., limiting) the rate of pressurization in a reconfigured pressurized flow system.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column. Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure (the mobile phase) through a column that is packed with a stationary phase composed of irregularly or spherically shaped particles, a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, etc.

Figure 1:
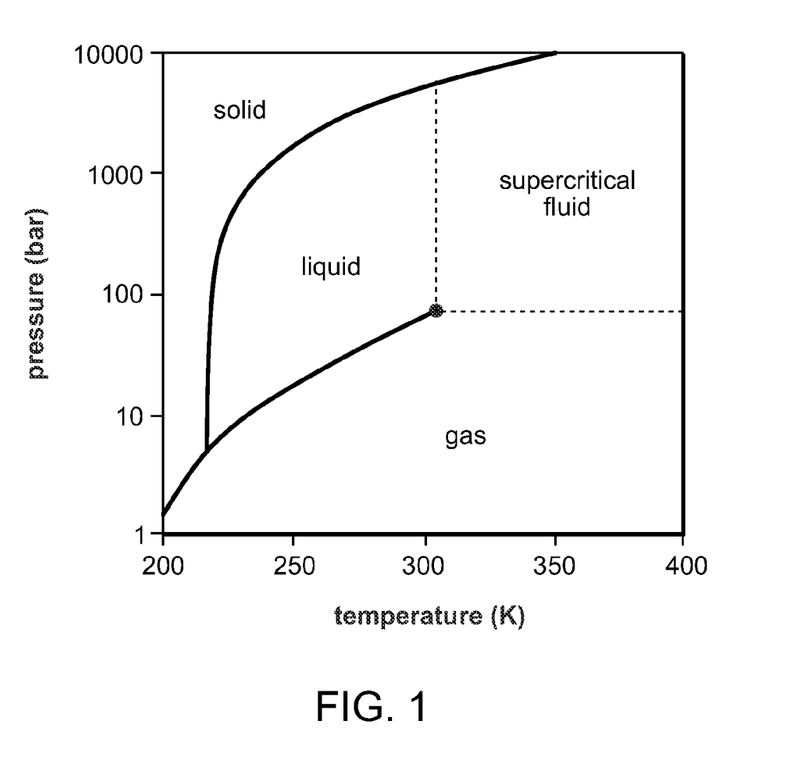
FIG. 1 is an exemplary graph of the physical state of a substance in relation to a temperature and pressure associated with the substance.

Supercritical Fluid Chromatography is another chromatographic technique, which has typically been used in preparative applications. For every liquid substance there is a temperature above which it can no longer exist as a liquid, no matter how much pressure is applied. Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

Because SFC typically uses $CO_2$, SFC processes are inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used.

SUMMARY

Exemplary embodiments of the present disclosure include systems, apparatuses, methods, and computer-readable storage mediums that are directed to limiting a rate of pressurization in a reconfigurable pressurized flow system, such as a reconfigurable $CO_2$-based chromatography system or other pressured flow systems. Different system configuration can have different system volumes, which can affect how quickly the system can be pressurized. Exemplary embodiments can implement one or more procedures or processes for limiting the rate pressurization for each of the possible configurations of the pressurized system based on a relationship between a measured closed system rate of pressurization and a set flow rate of the solvent through the system.

In one embodiment, a method of limiting a rate of pressurization in a pressurized flow system having a configurable system volume is disclosed. The method includes identifying a relationship between a flow rate of a solvent in the system and a closed system rate of pressurization of the system and generating a dynamic limit to restrict the rate of pressurization based on the relationship.

In another embodiment, a system for limiting a rate of pressurization of a pressurized flow system having a configurable system volume is disclosed. The system includes a column manager, a pump, a pressure regulator, and a controller. The column manager is configured to receive a column. The column effects a system volume for the system. The pump pumps a solvent through the system at a flow rate. The pressure regulator controls a rate of pressurization of the system. The controller is configured set the pressure regulator to a closed system rate of pressurization, measure the closed system rate of pressurization at the flow rate, determine a relationship between the closed system rate of pressurization and the flow rate, and to generate a dynamic limit for the rate of pressurization based on the relationship.

In yet another embodiment, a non-transitory computer readable storage medium storing instructions executable by a processing device is disclosed. Execution of the instructions causes the processing device to pump a solvent through the system at a flow rate, set a rate of pressurization to a closed system rate of pressurization, measure the closed system rate of pressurization at the flow rate, and determine a relationship between the closed system rate of pressurization and the flow rate. Execution of the instructions also causes the processing device to generate a dynamic limit for the rate of pressurization based on the relationship.

In some embodiments, the maximum possible system volume and a minimum flow rate for the system can be determined and the closed system rate of pressurization for the maximum possible volume of the system can be measured with the flow rate set to the minimum flow rate.

In some embodiments, the relationship can be a ratio and the relationship can be identified by computing the ratio between the closed system rate of pressurization and the minimum flow rate.

In some embodiments, the closed system rate of pressurization can be limited by applying a different flow rate during an operation of the system having a first system volume and the dynamic limit can be set based on the ratio and the different flow rate. The dynamic limit can be set independent of the first system volume.

In some embodiments, the ratio can be used to set the dynamic limit for each possible system volume.

In some embodiments, the relationship can be a ratio and the relationship can be identified by applying the flow rate in the system, measuring the closed system rate of pressurization at the flow rate, and computing a ratio between the closed system rate of pressurization and the flow rate.

In some embodiments, a different flow rate can be applied in the system and the dynamic limit can be set based on the ratio and the different flow rate.

In some embodiments, a substantially constant system volume can be maintained to compute the ratio.

In some embodiments, the flow rate changes according to a gradient.

In some embodiments, the ratio can be computed upon each activation of the system.

In some embodiments, the solvent can include carbon dioxide.

In some embodiments, the ratio can be computed in response to a user request.

In some embodiments, the ratio can be computed without knowing a configuration of the system and the system volume of the configuration.

In some embodiments, the rate of pressurization can be restricted by a valve assembly in a pressure regulator that is controlled by an actuator control signal.

One or more embodiments feature methods, processes or systems directed to providing improved control over pressure in a pressurized flow system. For example, in an embodiment, the methods or processes provide improved pressure control by detecting a volume of the pressurized flow system and relating the measured volume back to optimize control parameters. In particular, in $CO_2$-based chromatography systems, the ability of a pressure regulator to control pressure is strongly influenced by system volume. Methods, processes and systems advantageously provide stable control of pressure relating to a measured volume back to the controller for use in controlling pressurization. Any combination or permutation of embodiments is envisioned.

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION

SFC can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC, the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC processes have the ability to act both as substance carriers (like the mobile phases in GC), and dissolve substances readily (like the solvents used in LC). In addition to generally having lower viscosities and better diffusion profiles similar to those of certain gases, the mobile phase in SFC processes also generally have high densities and dissolving capacities similar to those of certain liquids. For example, SFs' high densities (0.2-0.5 $gm/cm^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. Since the diffusion of solutes in a SFC mobile phase is about ten times greater than that in liquids (about three times less than in gases), this results in a decrease in resistance to mass transfer in the column and allows for fast high resolution separation. Also, the solvation strength of the mobile phase in SFC processes is directly related to the fluid density. Thus, the solubility of solids can be easily manipulated by making slight changes in temperatures and pressures.

Another important property of the mobile phase in SFC processes is that it provides high resolution chromatography at much lower temperatures. For example, an analyte dissolved in supercritical $CO_2$ can be recovered by reducing the pressure and allowing the sample to evaporate under ambient laboratory conditions. This property is useful when dealing with thermally unstable analytes, such as high molecular weight biopolymers or proteins. The combination of one or more mechanical or column changes to an SFC instrument (e.g., a $CO_2$-based chromatography instrument) coupled with the inherent properties of the SFC itself, allows for the separation of both chiral and achiral compounds, and has become increasingly predominant in the field of preparatory separations for drug discovery and development. Despite considerable advances in SFC technology, there is a need to develop innovative methods and apparatuses that improve the use of SFC. Controlling and stabilizing the pressure in an SFC instrument by one or more process and/or improving one or more of the instrumental characteristics of the system, may lead to, amongst others, improved compound separation and efficiency.

For example, better resolution and increased flow rate would decrease cycle times (i.e., shorter cycle times) and allow for improved separation of both chiral and achiral compounds, and lead to an overall increase in laboratory efficiency; increased speed and throughput would decrease the amount of solvent and cost(s) associated with SFC; and the ability to further integrate SFC with other detection methods, such as Mass Spectrometry (MS), Flame Ionization Detectors (FID), and Ultraviolet/Visible (UV) detectors, would improve the mainstream use of SFC using a mobile phase including $CO_2$ as an eco-friendly, yet effective, alternative method for the fast, complete, and sensitive analysis of analytes.

Exemplary embodiments of the present disclosure are directed to limiting a rate of pressurization in a reconfigurable pressurized flow system, such as a reconfigurable $CO_2$-based chromatography system or other pressured flow systems. Different system configuration can have different system volumes. Exemplary embodiments can implement one or more procedures or processes for limiting the rate pressurization for each of the possible configurations of the pressurized system based on a relationship between a measured rate of pressurization and a set flow rate of the solvent through one or more of the system configuration.

As one example, a worst case system configuration can be used to determine the relationship. The system can be configured in the worst case system configuration by using a system configuration with the maximum system volume and operating the system at a set flow rate. For example, the flow rate can be set to a minimum flow rate so that the resolution of the measurements can be maximized. The rate of pressurization can be measured when the system is configured in a closed state (i.e., a valve of a dynamic pressure regulator is closed), which corresponds to a closed system rate of pressurization that can be achieved by the system for a set flow rate. The relationship between the measured closed system rate of pressurization, e.g., for the present embodiment, the rate of pressurization of a closed system at the minimum flow rate, and the minimum flow rate can be determined. The relationship generated using the worst case system configuration can be used to across different system configurations having different system volumes to generate a dynamic limit for the rate of pressurization for the different system configurations.

As another example, the relationship can be determined upon each activation of the system, when the system configuration is changed, and/or upon request from the user. To determine the relationship, a flow rate is set for a selected system configuration and the system is configured to set the rate of pressurization to a maximum rate of pressurization (i.e. the rate at which the closed system pressurizes for a set flow rate). The closed system rate of pressurization is measured at the set flow rate and the relationship between the measured closed system rate of pressurization and the set flow rate is determined. The relationship can be used to generate a dynamic limit for the rate of pressurization of the system having the selected system configuration.

As used herein, the term "rate of pressurization" refers to a rate at which a system pressurizes for a set flow rate. The rate of pressurization of a system can range from a minimum rate of pressurization to a maximum rate of pressurization.

As used herein, the terms "maximum rate of pressurization" or "closed system rate of pressurization" are used interchangeably herein to refer to a rate of pressurization of a closed system for a set flow rate, i.e. the highest rate at which the closed system can pressurize for a given flow rate.

As used herein, the terms "downstream" and "upstream" refer to relative locations in a system flow, wherein upstream refers to being associated with an earlier portion of the system flow compared to a later portion of the system flow and downstream refers to being associated with a later portion of the system flow compared to an earlier portion of the system flow.

Figure 2:
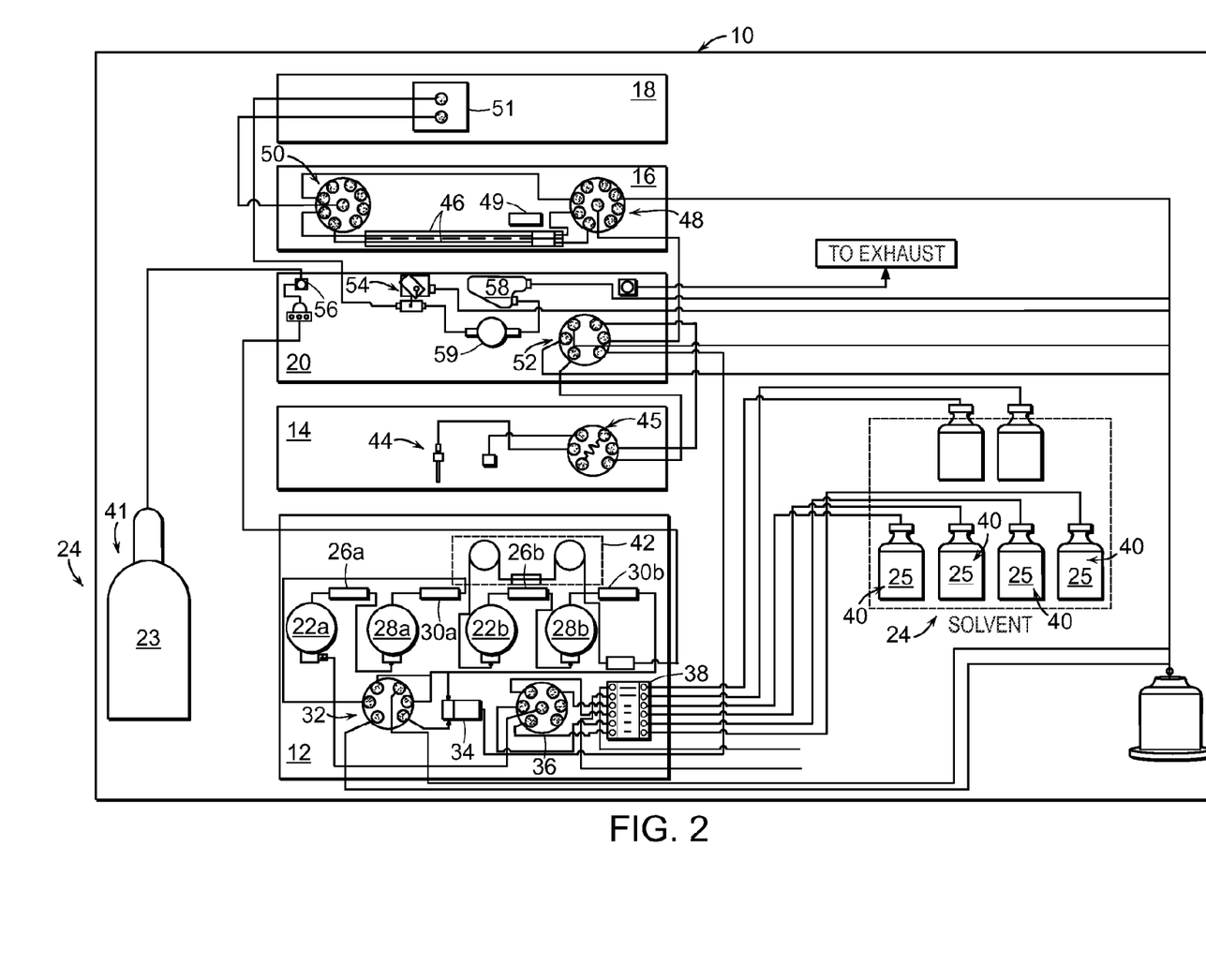
FIG. 2 is a block diagram of an exemplary pressurized flow system.

FIG. 2 is a block diagram of an exemplary pressurized flow system, which in the present embodiment is implemented as a $CO_2$-based chromatography system 10. While the present embodiment is illustrative of a $CO_2$-based chromatography system operated at or near supercritical conditions, those skilled in the art will recognize that exemplary embodiments of the present disclosure can be implemented as other pressurized flow systems and that one or more system components of the present disclosure can be implemented as components of other pressurized systems. The $CO_2$-based chromatography system 10 can be configured to detect sample components of a sample using chromatographic separation in which the sample is introduced into a mobile phase that is passed through a stationary phase. The system 10 can include one or more system components for managing and/or facilitating control of the physical state of the mobile phase, control of the pressure of the system 10, introduction of the sample to the mobile phase, separation of the sample into components, and/or detection of the sample components, as well as venting of the sample and/or mobile phase from the system 10.

Figure 3:
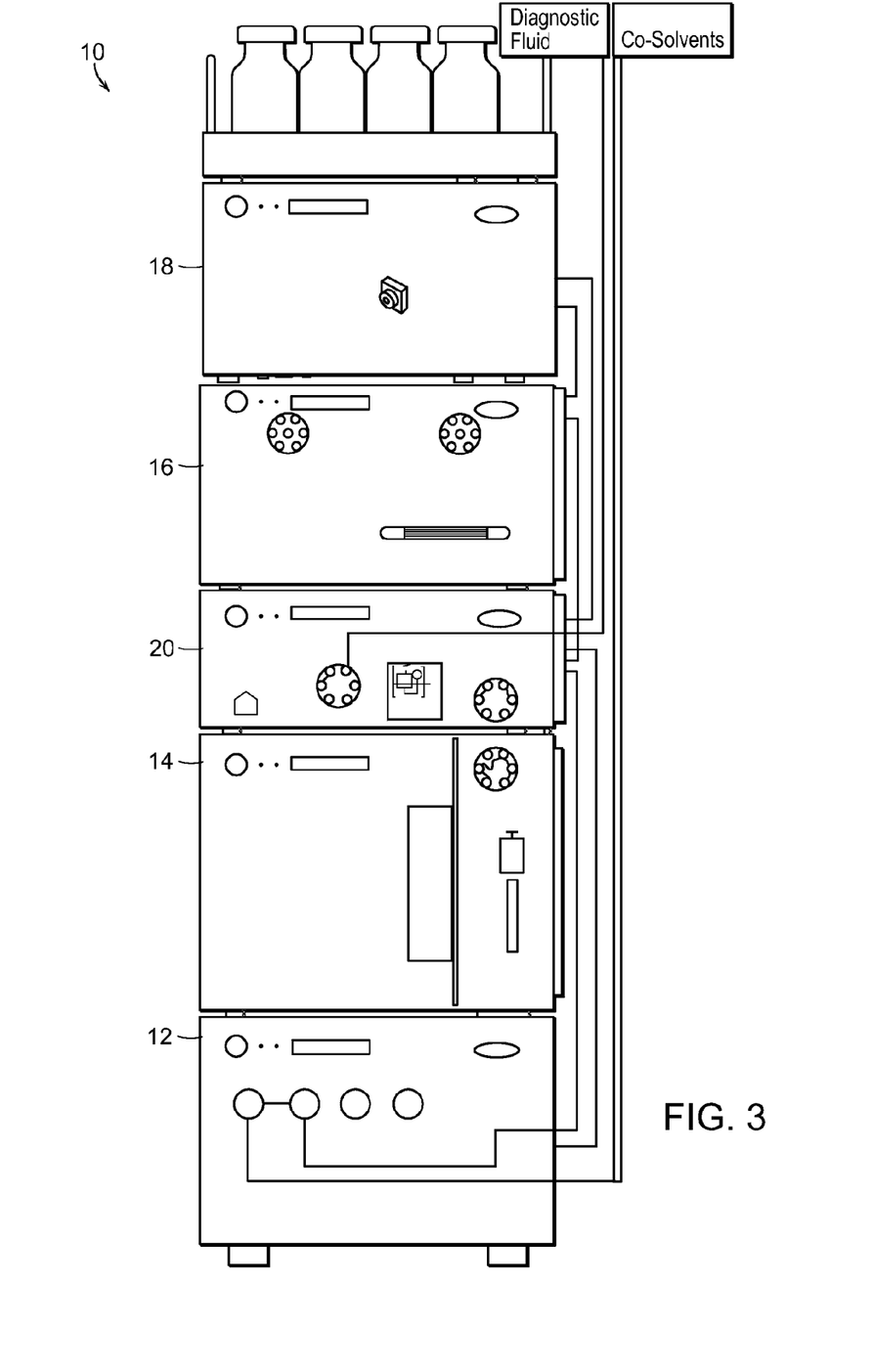
FIG. 3 is a block diagram of an exemplary arrangement of an embodiment of the system of FIG. 2.
Figure 4:
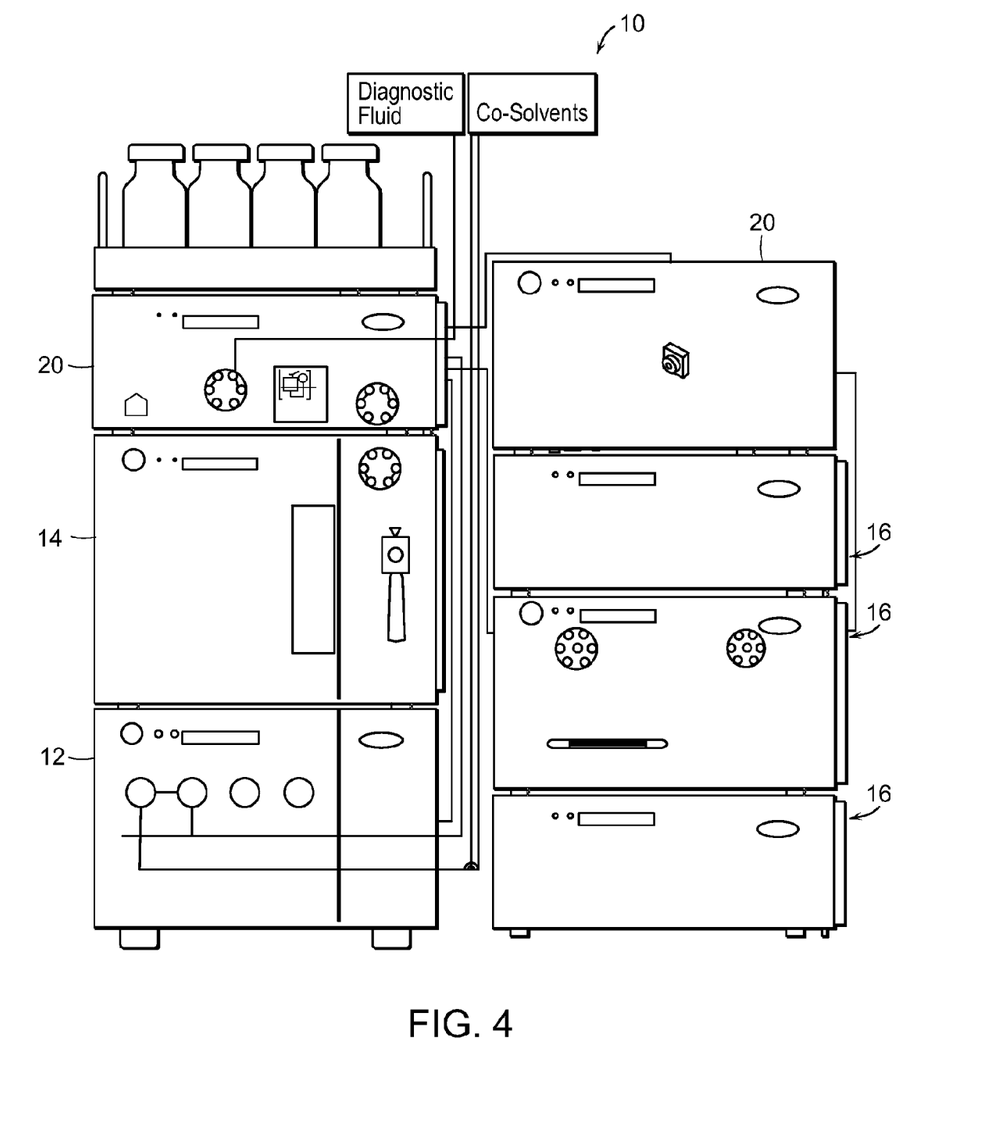
FIG. 4 is a block diagram of another exemplary arrangement of an embodiment of the system of FIG. 2.

In the present embodiment, the $CO_2$-based chromatography system 10 can include a solvent delivery system 12, a sample delivery system 14, a sample separation system 16, a detection system 18 (e.g., a PDA detector), and system/convergence manager 20. In some embodiments, the system components can be arranged in one or more stacks. As one example, in one embodiment, the system components of the system 10 can be arranged in a single vertical stack (FIG. 3). As another example, the system components of the system 10 can be arranged in multiple stacks (FIG. 4). Those skilled in the art will recognize that other arrangements of the components of the system 10 are possible. Furthermore, while embodiments of the system 10 have been illustrated as including system components 12, 14, 16, 18, and 20, those skilled in the art will recognize that embodiments of the system 10 can be implemented as a single integral unit, that one or more components can be combined, and/or that other configurations are possible.

The solvent delivery system 12 can include one or more pumps 22a, 22b configured to pump one or more solvents 24, such as mobile phase media 23 (e.g., carbon dioxide) and/or modifier media 25 (i.e., a co-solvent, such as, e.g., methanol, ethanol, 2-methoxyethanol, isopropyl alcohol, or dioxane), through the system 10 at a predetermined flow rate. For example, the pump 22a can be in pumping communication with the modifier media 25 to pump the modifier media 25 through the system 10, and the pump 22b can be in pumping communication with the mobile phase media 23 to pump the mobile phase media 23 through the system 10. An output of the pump 22a can be monitored by a transducer 26a and an output of the pump 22b can be monitored by a transducer 26b. The transducers 26a, 26b can be configured to sense the pressure and/or flow rate associated with the output of the solvent 24 from the pumps 22a, 22b, respectively.

The outputs of the pumps 22a, 22b can be operatively coupled to an input of accumulators 28a and 28b, respectively. The accumulators 28a, 28b are refilled by the outputs of the pumps 22a, 22b, respectively, and can contain an algorithm to reduce undesired fluctuations in the flow rate and/or pressure downstream of the pumps 22a and 22b, which can cause detection noise and/or analysis errors on the system 10. An output of the accumulator 28a can be monitored by a transducer 30a and an output of the accumulator 28b can be monitored by a transducer 30b. The transducers 30a, 30b can be configured to sense pressure and/or flow rate at an output of the accumulators 28a, 28b, respectively. The outputs of the accumulators 28a, 28b can be operatively coupled to a multiport valve 32, which can be controlled to vent the solvent 24 (e.g., mobile phase media 23 and modifier media 25) being pumped by the pumps 22a, 22b and/or to output the solvent 24 to a mixer 34. The mixer 34 can mix the modifier media 25 and the mobile phase media 23 output from the pumps 22a, 22b, respectively (e.g., after first passing through the accumulators 28a, 28b) and can output a mixture of the mobile phase media 23 and the modifier media 25 to form a solvent stream (i.e., mobile phase) that flows through the system 10. The output of the mixer 34 can be operatively coupled to the system/convergence manager 20 as discussed in more detail below.

In exemplary embodiments, the solvent delivery system 12 can include a multiport solvent selection valve 36 and/or a degasser 38. The solvent selection valve 36 and/or the degasser 38 can be operatively disposed between an input of the pump 22a and solvent sources, e.g., solvent containers 40, such that the solvent selection valve 36 and/or the degasser 38 are positioned upstream of the pump 22a. The solvent selection valve 36 can be controlled to select the modifier media 23 to be used by the system 10 from one or more solvent containers 40 and the degasser 38 can be configured to remove dissolved gases from the media modifier 23 before the media modifier 23 is pumped through the system 10.

In exemplary embodiments, the solvent delivery system 12 can include a pre-chiller 42 disposed between an input of the pump 22b and a solvent source, e.g., solvent container 41, such that the pre-chiller is disposed upstream of the input to the pump 22b and downstream of the solvent container 41. The pre-chiller 42 can reduced the temperature of the mobile phase media 23 before it is pumped through the system 10 via the pump 22b. In the present embodiment, the mobile phase media 23 can be carbon dioxide. The pre-chiller can decrease the temperature of the carbon dioxide so that the carbon dioxide is maintained in a liquid state (i.e., not a gaseous state) as it is pumped through at least a portion of the system 10. Maintaining the carbon dioxide in a liquid state can facilitate effective metering of the carbon dioxide through the system 10 at the specified flow rate.

The pumps 22a, 22b can pump the solvent 24 through the system 10 to pressurize the system 10 to a specified pressure, which may be controlled, at least in part, by the system/convergence manager 20. In exemplary embodiments, the system 10 can be pressurized to a pressure between about 700 psi and about 18,000 psi or about 1,400 psi and about 8,000 psi. In one embodiment, the system 10 can be pressurized to a pressure of about 6,000 psi. By pressurizing the system 10 at these pressure levels (such as those pressure levels described above), the solvent stream (i.e., mobile phase) can be maintained in a liquid state before transitioning to a supercritical fluid state or near supercritical state (e.g., highly compressed gas or compressible liquid) for a chromatographic separation in a column, which can be accomplished by raising the temperature of the pressurized solvent stream.

The sample delivery system 14 can select one or more samples to be passed through the system 10 for chromatographic separation and detection. The sample delivery system 14 can include a sample selection and injection member 44 and a multi-port valve 45. The sample selection and injection member 44 can include a needle through which the sample can be injected into the system 10. The multiport valve 45 can be configured to operatively couple the sample selection and injection member 44 to an input port of the system/convergence manager 20.

The sample separation system 16 can receive the sample to be separated and detected from the sample delivery system 14, as well as the pressurized solvent stream from the solvent delivery system 12, and can separate components of the sample passing through the system 10 to facilitate detection of the samples using the detection system 18. The sample separation system 16 can include one or more columns 46 disposed between an inlet valve 48 and an outlet valve 50. The one or more columns 46 can have a generally cylindrical shape that forms a cavity, although one skilled in the art will recognize that other shapes and configurations of the one or more columns is possible. The cavity of the columns 46 can have a volume that can at least partially be filled with retentive media, such as hydrolyzed silica, such as $C_8$ or $C_{18}$, or any hydrocarbon, to form the stationary phase of the system 10 and to promote separation of the components of the sample. The inlet valve 48 can be disposed upstream of the one or more columns can be configured to select which of the one or more columns 46, if any, receives the sample. The outlet valve 50 can be disposed downstream of the one or more columns 46 to selective receive an output from the one or more columns 46 and to pass the output of the selected one or more columns 46 to the detection system 18. The columns 46 can be removeably disposed between the valves 48, 50 to facilitated replacement of the one or more columns 46 new columns after use. In some embodiments, multiple sample separation systems 16 can be included in the system 10 to provide an expanded quantity of columns 46 available for use by the system 10 (FIG. 4).

In exemplary embodiments, the sample separation system 16 can include a heater 49 to heat the pressurized solvent stream 24 prior and/or while the pressured solvent stream 24 passes through the one or more columns 46. The heater 49 can heat the pressurized solvent stream to a temperature at which the pressured solvent transition from a liquid state to a supercritical fluid state so that the pressurized solvent stream passes through the one or more columns 46 as a supercritical fluid.

Referring again to FIG. 2, the detection system 18 can be configured to receive components separated from a sample by the one or more columns 46 and to detect a composition of the components for subsequent analysis. In an exemplary embodiment the detection system 18 can include one or more detectors 51 configured to sense one of more characteristics of the sample components. For example, in one embodiment, the detectors 51 can be implemented as one or more photodiode arrays.

The system/convergence manager 20 can be configured to introduce a sample from the sample delivery system 14 into the pressurized solvent stream flowing from the solvent delivery system 12 and to pass the solvent stream and sample to the sample separation system 16. In the present embodiment, the system/convergence manager 20 can include a multiport auxiliary valve 52 which receives the sample injected by the sample delivery system 14 through a first inlet port and the pressurized solvent stream from the solvent delivery system 12 through a second inlet port. The auxiliary valve 52 can mix the sample and the solvent stream and output the sample and solvent stream via an outlet port of the multiport auxiliary valve 52 to an inlet port of the inlet valve 48 of the sample separation system 16.

The system/convergence manager 20 can also be configured to control the pressure of the system 10 and to facilitate cooling, heating, and/or venting of the solvent from the system 10, and can include a vent valve 54, a shut off valve 56, a back pressure regulator 58, and a transducer 59. The vent valve 54 can be disposed downstream of the detection system 18 can be configured to decompress the system 10 by venting the solvent from the system 10 after the solvent has passed through the system 10. The shut off valve 56 can be configured to disconnect the solvent supply from the inlet of the pump 22b of the solvent delivery system to prevent the solvent from being pumped through the system 10.

The back pressure regulator 58 can control the back pressure of the system 10 to control the flow of the mobile phase and sample through the column, to maintain the mobile phase in the supercritical fluid state (or, in some embodiments, in a near supercritical state, such as, a highly-compressed gas or compressible liquid) as the mobile phase passes through the one or more columns 46 of the sample separation system 16, and/or to prevent the back pressure from forcing the mobile phase reversing its direction a flow through the one or more columns 46. Embodiments of the back pressure regulator 58 can be configured to regulate the pressure of the system 10 so that the physical state of the solvent stream (i.e., mobile phase) does not change uncontrollably upstream of and/or within the back pressure regulator 58. The transducer 59 can be a pressure sensor disposed upstream of the back pressure regulator 58 to sense a pressure of the system 10. The transducer 59 can output a feedback signal to a processing device which can process the signal to control an output of an actuator control signal from the processing device.

Figure 5:
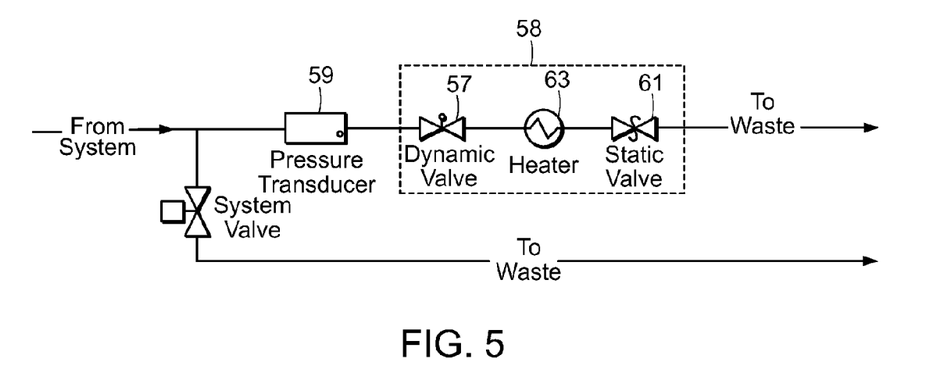
FIG. 5 is a flow diagram of a mobile phase through a system manager portion of the an exemplary embodiment of the pressurized flow system.

In exemplary embodiments, as shown in FIG. 5, the back pressure regulator 58 can include a dynamic pressure regulator 57, a static pressure regulator 61, and a heater 63. The static pressure regulator 61 can be configured to maintain a predetermined pressure upstream of the back pressure regulator 58. The dynamic pressure regulator 57 can be disposed upstream of the static pressure regulator 61 and can be configured to set the system pressure above the predetermined pressure maintained by the static regulator 61. The heater 63 can be disposed downstream of the dynamic pressure regulator 57 and can be disposed in close proximity to the static pressure regulator 61 to heat the solvent stream as it passes through the static pressure regulator 61 to aid in control of the physical state of the solvent as it passes through the static pressure regulator. The structure, function, and/or operation of the back pressure regulator 58, static pressure regulator, and/or dynamic regulator are described in more detail below.

In summary, an exemplary operation of the $CO_2$ based chromatography system 10 can pump mobile phase media 23 and modifier media 25 at a specified flow rate through the system 10 as a solvent stream (i.e., mobile phase) and can pressurize the system 10 to a specified pressure so that the solvent stream maintains a liquid state before entering the sample separation system 16. A sample can be injected into the pressurized solvent stream by the sample delivery system 14, and the sample being carried by the pressurized solvent stream can pass through the sample separation system 16, which can heat the pressurized solvent stream to transition the pressurized solvent stream from a liquid state to a supercritical fluid state. The sample and the supercritical fluid solvent stream can pass through at least one of the one or more columns 46 in the sample separation system 16 and the column(s) 46 can separate components of the sample from each other. The separated components can pass the separated components to the detection system 18, which can detect one or more characteristics of the sample for subsequent analysis. After the separated sample and solvent pass through the detection system 18, the solvent and the sample can be vented from the system 10 by the system/convergence manager 20.

In other embodiments, the $CO_2$ based chromatography system described herein can also be used for preparatory methods and separations. Typical parameters, such as those described above, may be manipulated to achieve effective preparatory separations. For example, the $CO_2$ based chromatography system described herein confers the benefit of exerting higher flow rates, larger columns, and column packing size, each of which contributes to achieving preparatory separation and function, while maintaining little or no variability in overall peak shape, peak size, and/or retention time(s) when compared to respective analytical methods and separations thereof. Thus, in one embodiment, the present disclosure provides $CO_2$ based chromatography systems, which are amendable to preparatory methods and separations with high efficiency and correlation to analytical runs.

Figure 6:
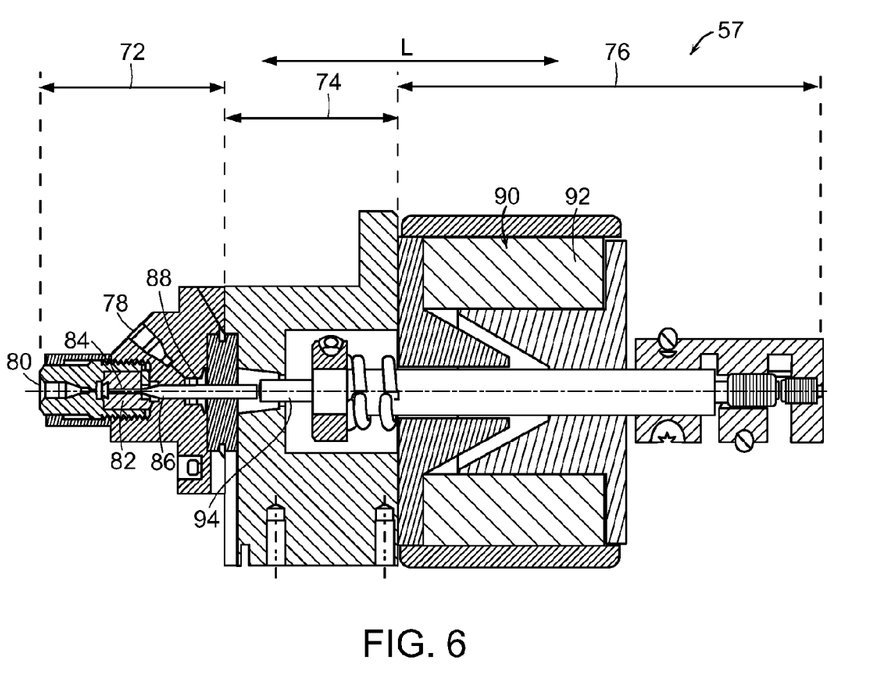
FIG. 6 is a cross-sectional view of a valve assembly for an exemplary dynamic pressure regulator in an exemplary embodiment of the pressurized system.

FIG. 6 is a cross-sectional view of an exemplary embodiment of a dynamic pressure regulator 57 along a longitudinal axis L of the dynamic pressure regulator. The dynamic pressure regulator 57 can be implemented as a valve assembly that includes a proximal head portion 72, an intermediate body portion 74, and a distal actuator portion 76. The head portion 72 of the valve assembly can include an inlet 78 to receive the pressurized solvent stream and an outlet 80 through which the pressurized solvent stream is output such that the solvent stream flows through the head portion from the inlet 78 to the outlet 80. A seat 82 can be disposed within the head portion 72 and can include a bore 84 through which the solvent stream can flow from the inlet 78 to the outlet 80 of the head.

A needle 86 extends into the head portion 72 from the body portion 74 of the valve assembly through a seal 88. A position of the needle 86 can be controlled with respect to the seat 82 to selectively control a flow of the solvent stream from the inlet 78 to the outlet 80. In exemplary embodiments, the position of the needle 86 can be used to restrict the flow through the bore 84 of the seat 82 to increase the pressure of the system 10 and can selectively close the valve by fully engaging the seat 82 to interrupt the flow between the inlet 78 and the outlet 80. When the valve is closed, the system 10 is a closed system. By controlling the flow of the solvent stream through the head portion based on the position of the needle 86, the pressure of the system 10 can be increased or decreased. For example, the pressure of the system can generally increase as the needle 86 moves towards the seat 82 along the longitudinal axis L and can generally decrease as the needle 86 moves away from the seat 82 along the longitudinal axis L.

The actuator portion 76 can include an actuator 90, such as a solenoid, voice coil, and/or any other suitable electro-mechanical actuation device. In the present embodiment, the actuator 90 can be implemented using a solenoid having a main body 92 and a shaft 94. The shaft 94 can extend along the longitudinal axis L and can engage a distal end of the needle 86 such that the needle 86 and shaft can form a valve member. A position of the shaft 94 can be adjustable with respect to the main body 92 along the longitudinal axis L and can be controlled by a coil (not shown) of the main body 92, which generates a magnetic field that is proportional to an electric current passing through the coil and a load applied to the shaft. The electric current passing through the coil can be controlled in response to an actuator control signal received by the actuator 90. In some embodiments, the actuator control signal can be a pulse width modulated (PWM) signal and/or the actuator control signal can be determined, at least in part, by the feedback signal of the pressure transducer 59.

The position of the shaft 94 can be used to move the needle 86 towards or away from the seat 82 to increase or decrease pressure, respectively. In exemplary embodiments, a position of the shaft 94, and therefore a position of the needle 86 with respect to the seat 82 can be controlled and/or determined based on an amount of electric current flowing through the solenoid. For example, the greater the electrical current the closer the needle 86 and shaft 94 are from the seat and the lower the pressure is in the system 10. The relationship between a position of the shaft 94 and the electric current flowing through the coil can be established through characterization of the actuator 90. The force imposed by the load on the solenoid can be proportional to the magnetic field. Similarly, the magnetic field can be proportional to the electric current flowing through the coil of the solenoid. For embodiments in which the actuator control signal is implemented as a PWM control signal, the pressure through the regulator 57 (e.g., force balance between needle 86 and shaft 94) can be set by a correlation to the duty cycle of the PWM control signal, e.g., a percentage of the duty cycle corresponding to an "on" state. For example, an increase in the duty cycle (i.e. an increase in the percentage of the duty cycle in the "on" state) can result in moving the needle 86 towards the bore 84 proportionally to increase the pressure or rate of pressurization and a decrease in the duty cycle (i.e. an decrease in the percentage of the duty cycle in the "on" state) can result in moving the needle 86 away from the bore 84 proportionally to decrease the pressure or rate of pressurization of the system 10.

Figure 7:
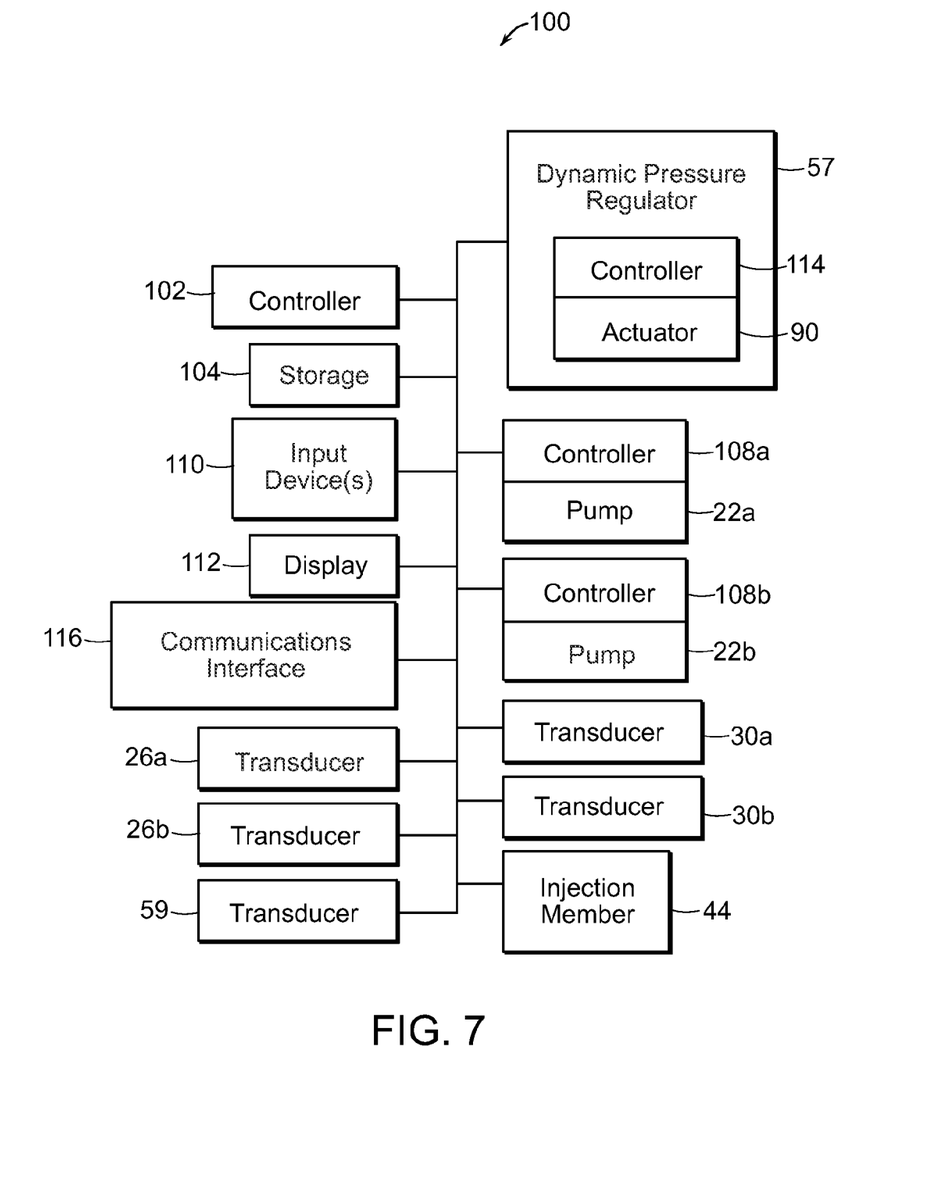
FIG. 7 is a block diagram of an exemplary control system that can be implemented to control an operation of an exemplary embodiment of the pressurized flow system.

FIG. 7 is a block diagram of an exemplary control system 100 that can be implemented to control the pressure of the system 10. The control system 100 can include a controller 102 in electrical communication with a storage device 104 (e.g., memory and/or other computer-readable storage mediums). The controller 102 can be implemented as a microcontroller, microprocessor, field programmable gate array (FPGA), and/or other processing devices. The storage 104 can be implemented as one or more non-transitory computer readable storage mediums including, for example, magnetic storage disks, optical disks, flash or solid state storage, and/or any other nonvolatile or volatile storage medium including random access memory, such as DRAM, SRAM, EDO RAM, MRAM, and the like. The storage 106 can store information corresponding to the system 10 and/or components thereof. The storage 106 can also store instructions that are executable by the controller 102 to control an operation of system 10 including an operation of the dynamic back pressure regulator 57. The controller 102 can also be in communication with one or more of the pumps 22a, 22b, one or more of the transducers 26a, 26b, 30a, 30b, 59, the injection member 44, the dynamic pressure regulator 57, input devices 110, and/or a display 112. In this embodiment, the pumps, 22a, 22b can be associated with pump controllers 108a, 108b, respectively, and the actuator 90 of the dynamic pressure regulator 57 can be associated with an actuator controller 114.

The controller 102 can receive signals from and/or transmit signals to the transducers 26a, 26b, 30a, 30b, 59, the injection member 44, the pump controllers 108a, 108b, one or more input devices 110, such as a keyboard, mouse, or other suitable input devices, the display 112, and the actuator controller 114, and/or other devices, such as other controllers (e.g., processing devices), computing devices (e.g., a Laptop, PC, mainframe), networked devices (e.g., servers, databases), and the like, which can be communicatively coupled to the controller 102 via, for example, a communication interface 116. In exemplary embodiments, the controller 102 can process the received signals and can control an operation of the pumps 22a, 22b, the injection member 44, and/or the actuator 90 in response to the signals.

In exemplary embodiments, embodiments of the system 10 can have one or more system configurations such that, e.g., the system can be configured to have different system volumes and/or can be configured to use different materials for the stationary phase. For example, in some embodiments, columns 46 used in the system can have different volumes and/or can be packed with a different retentive material. For embodiments of the system 10 is implemented as a system 10, the ability of the back pressure regulator to control the pressure of the system can be influenced by the system volume and/or other factors. In such embodiments, the influence of the system volume on the back pressure regulator can result from, for example, an inability of the fluid system (e.g., pumps to operate as fast as or faster than the mechanics (e.g., valves)). In such embodiments, permitting the system 10 to be reconfigurable can have adverse effects on an operation of the system because a rate of pressurization can be affected differently by the possible system configurations. For example, a system volume, solvent flow rate, a compressibility of the solvent, and/or the temperature of the system 10 including, for example, the column 46 and retentive media within the column 46 (which can affect the compressibility of the solvent) can affect the rate at which the system can be pressurized. The rate of pressurization can be one factor for determining a stability of the pressure control in the system.

In exemplary embodiments, the system 10 can be configured to account for the different possible system configurations to determine an acceptable rate of pressurization for a particular system configuration. For example, embodiments of the controller 102 of an embodiment of the $CO_2$-based chromatography system can be configured to limit an output of the actuator control signal to limit the rate of pressurization of the system so that the rate of pressurization of the system does not exceed a dynamic limit for the rate of pressurization associated with the system configuration being used. In one embodiment, a relationship between a flow rate of the solvent through the system and a closed system rate of pressurization of the system can be identified when the valve of the dynamic pressure regulator is closed (i.e. when the needle 86 engages the bore 84 so that the rate of pressurization is for a closed system). Once the relationship is identified, the identified relationship can be used during an operation of the system to limit the rate of pressurization of the system based on set flow rate.

Figure 8:
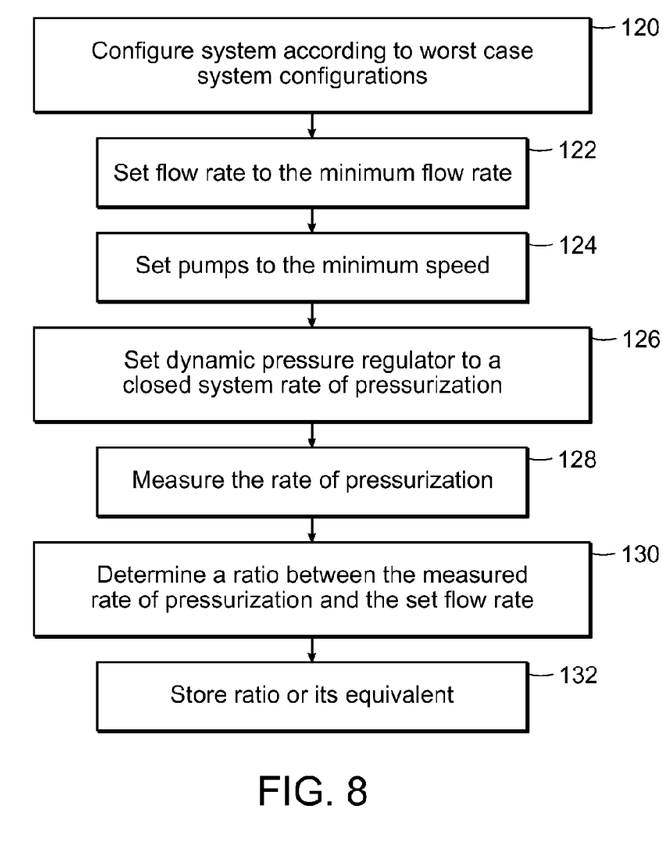
FIG. 8 is a flowchart illustrating an exemplary process to limit a rate of pressurization of an exemplary embodiment of the pressurized flow system using an exemplary embodiment of a control system.

FIG. 8 is a flowchart illustrating an exemplary process to limit a rate of pressurization of the system using an embodiment of the control system 100 (e.g., a limit generation process). To begin the system is configured according to a worst case system configuration (120). As one example, the worst case system configuration can be a configuration having a maximum system volume and a minimum flow rate. The maximum possible system volume is determined and the system is configured to have the maximum possible system volume. Since temperature can affect the compressibility of the solvent, which may affect the rate at which the system is pressurized, it may be desirable in some embodiments to allow the system to reach thermal stability before continuing the limit generation process. In some embodiments, the limit generation process can be performed without allowing the system to reach thermal stability. A minimum flow rate of the solvent through the system is determined based on a minimum speed at which one or more of the pumps can be operated (122) and the one or more pumps are set to the minimum speed to pump the solvent through the system at the minimum flow rate (124). For example, the control system can output one or more pump control signals to the pump controllers and the pump controllers can set the speed of the pumps to the minimum speed based on the one or more pump control signals. The dynamic regulator can be set to implement a closed system rate of pressurization in the system (126). For example, the control system can output an actuator control signal to controller of the actuator to bias the valve member (e.g., the needle 86 and shaft 94) towards the seat 82 to engage the bore 84 and close the valve such the flow of the solvent through the dynamic pressure regulator is interrupted. By closing the valve of the dynamic regulator, the controller can ensure that the system is closed and the rate of pressurization in the system is the closed system rate of pressurization at the minimum flow rate.

As the solvent is pumped through the closed system, the rate of pressurization of the system can be measured via one or more of the transducers in the system (128) and a ratio between the measured closed system rate of pressurization (e.g., the maximum rate of pressurize for the particular system configuration in its closed state at the set flow rate) and the set flow rate (e.g., the minimum flow rate of the system) can be determined (130). In exemplary embodiments, the control system can receive the feedback signal from the transducer 59 that corresponds to the rate of pressurization of the closed system and can determine the rate of pressurization based on the feedback signal. The control system can also determine the pump control signal being output to the pump controllers, which corresponds to the set flow rate of the solvent through the system. Using this information, the control system can determine the closed system rate of pressurization (e.g., the maximum rate of pressurization) and the set flow rate (e.g., the minimum flow rate) and can compute the ratio (e.g., by dividing the measured closed system rate of pressurization by the set flow rate). Alternatively, the ratio can be computed by another device such as a computing device. The ratio or its equivalent can be stored in a non-transitory computer readable storage medium (e.g., storage 104) of the control system for subsequent use (132). For embodiments in which the system does not reach thermal stability before the limit generation process is performed, the system can be programmed to adjust the ratio to account for the affect the temperature of the system can have on the rate of pressurization. As such, the system can store a ratio that provides a conservative approximation that attempts to take into account the effect of temperature on the system.

The ratio or its equivalent generated using the limit generation process of FIG. 8 can be used to generate a dynamic limit for an operational rate of pressurization of the system during operation and across the possible system configurations, such that the ratio can be used to limit the operational rate of pressurization independent of the possible system configurations and possible system volumes associated with the system configurations. That is, the operational rate of pressurization can be limited for the different possible system configurations based on the ratio generated from the worst case system configuration and without knowledge of the system volume associated with a system configuration selected for use. For example, the ratio generated using the limit generation process of FIG. 8 can be used to provide a dynamically determined upper limit on the operational rate of pressurization based on a set flow rate for each of the possible system configurations. Thus, the system can limit the operational rate of pressurization of the system based on the set flow rate without identifying, and regardless of, which system configuration is being implemented. The ratio, allows users of the system to change the system configuration without requiring the user to determine the system volume associated with the implemented system configuration and to determine an appropriate limit for each of the possible system configurations.

After the ratio is generated using the exemplary limit generation process of FIG. 8, a dynamic limit can be generated for the operational rate of pressurization of a selected system configuration from the one or more possible system configurations. The dynamic limit can be dependent on the flow rate that is set for the selected system configuration, such that when the flow rate changes, the dynamic limit changes. For example, if the flow rate is increased during operation, the dynamic limit can be increased proportionally to maintain the ratio generated using the limit generation process. Thus, the upper limit for the operational rate of pressurization of the system can be dynamically generated during an operation of the system, but the ratio remains fixed using the limit generation process. In exemplary embodiments, the limit for the operational rate of pressurization can be controlled based on a position of the needle 86 with respect to the bore 84 such that the actuator control signal can limit the rate of pressurization.

Figure 9:
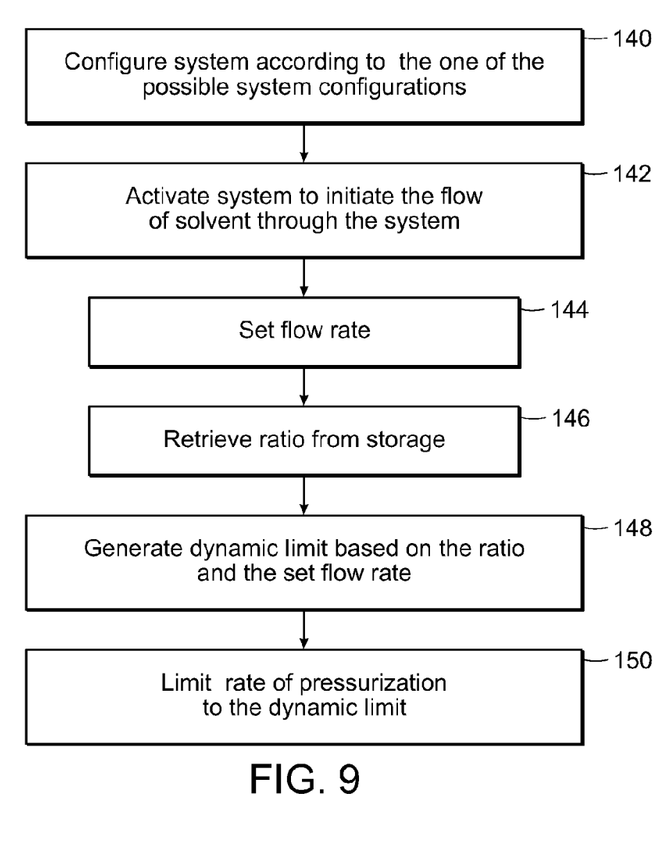
FIG. 9 is a flowchart illustrating an exemplary operation of an embodiment of the pressurized flow system based on the process described in FIG. 8.

FIG. 9 is a flowchart illustrating an operation of the system based on the ratio generated in FIG. 8. To begin the system can be configured according to the one of the possible system configurations having a system volume (140) and can be activated to initiate the flow of solvent through the system (142). The flow rate of the solvent can be set to one or more values (e.g., any flow rate between the minimum flow rate and the maximum flow rate) during the operation of the system (144). In response to the set flow rates, a ratio can be retrieved from the storage (146) and the dynamic limit for the operational rate of pressurization can be generated based on the ratio and the set flow rate (148). As an illustrative example, if the ratio is 2:1 (e.g., characterized rate of pressurization is twice that of flow rate as determined by FIG. 8), the dynamic limit for the operational rate of pressurization can be twice the set flow rate. The system can limit the rate of pressurization to the dynamic limit such that the rate of pressurization cannot exceed the dynamic limit (150).

In some embodiments, the ratio retrieved from storage can be determined based on the worst case system configuration using the limit generation process of FIG. 8 such that each possible system configuration uses the same ratio. In some embodiments, the ratio retrieved from storage can be for the specific system configuration being implemented by the user as described in FIG. 10 below. In some embodiments, the ratio can be from any one of the possible system configurations. If the ratio retrieved from storage does not correspond to the worst case system configuration or the specific system configuration being implemented, the user may be prompted to provide information about the particular system configuration being used (e.g., the system volume, type of retentive media, type of solvent, etc.). The system can use the information provided by the user in conjunction with information corresponding the system configuration used to obtain the ratio (e.g., system volume, type of retentive media, type of solvent, etc.) to generate a new ratio for the particular system configuration being implemented by the user. As one example, a volume ratio of the system volumes can be determine (i.e. the ratio between the volume of the particular system configuration and the volume of the system configuration used to generate the ratio retrieved from storage) and the ratio retrieved from storage can be adjusted based on the volume ratio. The difference between the ratio retrieved from storage and the new ration can be inversely proportional to the difference in the system volumes. For example, if the system volume increases by a factor of two, the ratio retrieved from storage is divided half.

To limit the rate of pressurization to the dynamic limit, the actuator control signal output by the control system (e.g., a PWM signal and associated duty cycle) can be controlled such that the operation of the dynamic pressure regulator cannot exceed, but can be less than, the dynamic limit determined based on the ratio and set flow rate. Thus, the rate of pressurization of the system can be set to any rate that is below the dynamic limit. By controlling the actuator control signal, the position of the valve member (e.g., the needle 86 and shaft 94) of the dynamic pressure regulator can be controlled so that the rate of pressurization is limited according to the ratio.

Figure 10:
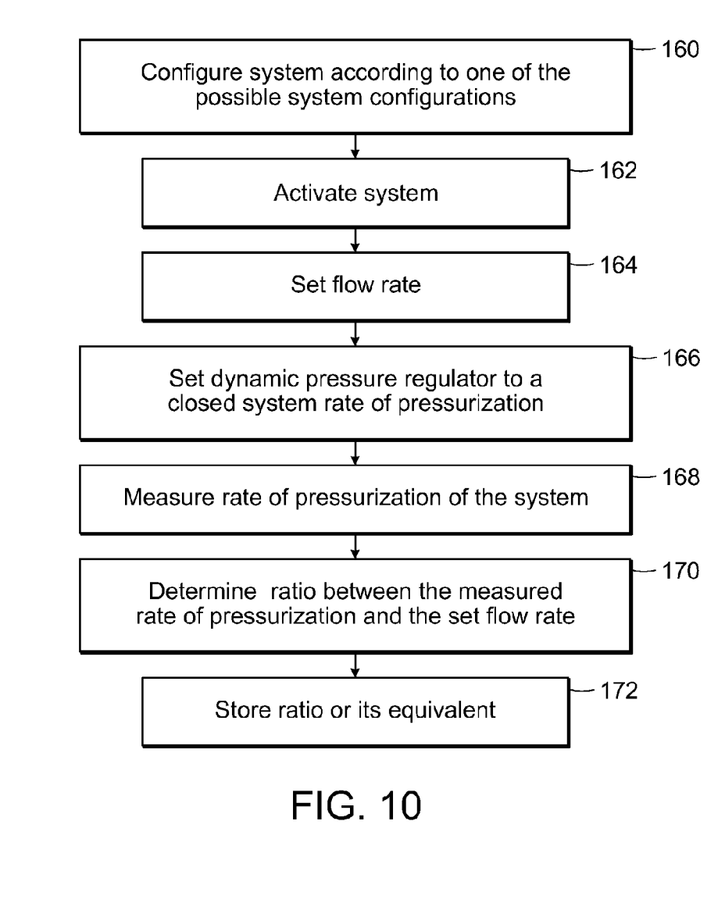
FIG. 10 is a flowchart illustrating another exemplary process to limit a rate of pressurization of an exemplary embodiment of the pressurized flow system using an exemplary embodiment of a control system.

FIG. 10 is a flowchart illustrating another exemplary process to limit a rate of pressurization of the system using an embodiment of the control system 100 (e.g., a limit generation process). The process of FIG. 10 can be implemented when the system is activated and/or when requested by a user. To begin the system is configured according to one of the possible system configurations (160) and the system is activated (162). Since temperature can affect the compressibility of the solvent, which may affect the rate at which the system is pressurized, it may be desirable in some embodiments to allow the system to reach thermal stability before continuing the limit generation process. In some embodiments, the limit generation process can be performed without allowing the system to reach thermal stability. A flow rate of the solvent through the system is set based on a speed at which one or more of the pumps is operated, which can be controlled by the control system of the system (164). For example, the control system can output one or more pump control signals to the pump controllers and the pump controllers can set the speed of the pumps to set the flow rate of the solvent through the system. The flow rate can be set to a constant value or can be set according to a gradient such that the flow rate increases or decreases according to the gradient. The system volume can substantially constant during the process, e.g., when the closed system rate of pressurization is being measured for the set flow rate. The dynamic regulator can be set to control the rate of pressurization in the system to a closed system rate of pressurization (166). For example, the control system can output an actuator control signal to the controller of the actuator to bias the valve member (e.g., the needle 86 and shaft 94) towards the seat 82 to engage the bore 84 and close the valve such the flow of the solvent through the dynamic regulator is interrupted and the system is in a closed state. By closing the valve of the dynamic regulator, the controller can ensure that the system is closed and the rate of pressurization in the system is the closed system rate of pressurization at the set flow rate.

As the solvent is pumped through the closed system, the rate of pressurization of the system can be measured via one or more of the transducers in the system (168) and a ratio between the measured rate of pressurization (e.g., the closed system rate of pressurization for the particular system configuration at the set flow rate) and the set flow rate can be determined (170). In exemplary embodiments, the control system can receive the feedback signal from the transducer 59 that corresponds to the rate of pressurization of the closed system and can determine the rate of pressurization based on the feedback signal. The control system can also determine the pump control signal being output to the pump controllers, which corresponds to the set flow rate of the solvent through the system. Using this information, the control system can determine the rate of pressurization (e.g., the closed system rate of pressurization) and the set flow rate and can compute the ratio (e.g., by dividing the measure rate of pressurization by the set flow rate). Alternatively, the ratio can be computed by another device such as a computing device. The ratio or its equivalent can be stored in a non-transitory computer readable storage medium (e.g., storage 104) of the control system for subsequent use (172). For embodiments in which the system does not reach thermal stability before the limit generation process is performed, the system can be programmed to adjust the ratio to account for the affect the temperature of the system can have on the rate of pressurization. As such, the system can store a ratio that provides a conservative approximation that attempts to take into account the effect of temperature on the system.

A ratio or its equivalent can be generate by the system each time a system configuration of the system changes, each time the system is activated, and/or upon request by the user, such that the ratio generated can be dependent on which of the possible system configurations is selected and the system volume associated with the selected system configuration. However, the system can generate the ratio and limit the operational rate of pressurization of the system without identifying which system configuration has been selected. In exemplary embodiments, the ratio can be deleted from the storage when the system is powered down and/or can be written over each time the system performs the process of FIG. 10. In one embodiment, the storage can include volatile memory for storing the ratio such that when the system is powered down the memory does not retain the ratio. The ratio generated using the limit generation process of FIG. 10 can be used to provide an upper limit on the operational rate of pressurization for the selected system configuration and can allow users of the system to change the system configuration without requiring the user to determine the system volume associated with the selected system configuration and to determine a limit of the operational rate of pressurization for each of the possible system configurations.

After the ratio is generated using the exemplary limit generation process of FIG. 10, a dynamic limit can be generated for the operational rate of pressurization of a selected system configuration. The dynamic limit can be dependent on the flow rate that is set for the system, such that when the flow rate changes, the dynamic limit changes. For example, if the flow rate is increased during operation, the dynamic limit can increase proportionally to maintain the ratio generated using the limit generation process of FIG. 10. Thus, the upper limit for the operational rate of pressurization of the system can be dynamically generated during an operation of the system, but the ratio remains fixed using the limit generation process.

Figure 11:
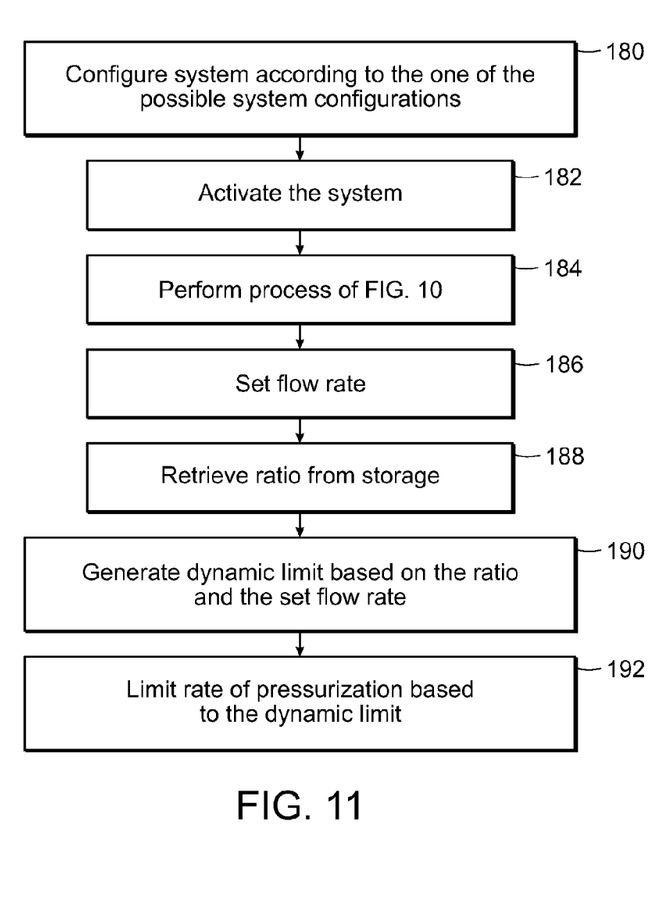
FIG. 11 is a flowchart illustrating an exemplary operation of an exemplary embodiment of the pressurized flow system based on the process described in FIG. 10.

FIG. 11 is a flowchart illustrating an operation of the system based on the ratio generated in FIG. 10. To begin, the system can be configured according to the one of the possible system configurations having a system volume (180) and can be activated to initiate the flow of solvent through the system (182). Upon activation of the system or upon request from the user, the system performs the process of FIG. 10 to generate the ratio (184). The flow rate of the solvent can be set to one or more values (e.g., any flow rate between the minimum flow rate and the maximum flow rate) during the operation of the system (186). In response to the set flow rates, the ratio can be retrieved from the storage (188) and the dynamic limit can be generated based on the ratio and the set flow rate (190). The system limits the operational rate of pressurization using the dynamic limit such that the operational rate of pressurization cannot exceed the dynamic limit (192).

To limit the operational rate of pressurization, the actuator control signal output by the control system (e.g., a PWM signal and associated duty cycle) can be controlled such that the operation of the dynamic pressure regulator cannot exceed, but can be less than, the dynamic limit determined based on the ratio and set flow rate. Thus, the operational rate of pressurization of the system can be set to any rate that is below the dynamic limit for the system. By controlling the actuator control signal, the position of the valve member (e.g., the needle 86 and shaft 94) of the dynamic pressure regulator can be controlled so that the operational rate of pressurization is limited according to the ratio.

While exemplary embodiments limit the operational rate of pressurization of the system as described above, those skilled in the art will recognize that the operational rate of pressurization can be limited based on one or more other techniques. For example, in one embodiment, the controller can determine the system volume based on system identification using the controller output and the input response. There are many methods of system identification that could be used by those familiar in the art. A second continuous method is to perform tests between injections to determine the system properties during operation without interfering with analysis.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer elements than those illustrated in the exemplary flowcharts, and that the elements in the exemplary flowcharts may be performed in a different order than the order shown in the illustrative flowcharts.

The invention claimed is:

1. A method of limiting a rate of pressurization in a pressurized flow system having a configurable system volume, the method comprising:

identifying a relationship between a flow rate of a solvent in the system and a closed system rate of pressurization of the system;

generating a dynamic limit to restrict the rate of pressurization based on the relationship;

determining a maximum possible system volume and a minimum flow rate for the system; and measuring the closed system rate of pressurization for the maximum possible system volume with the flow rate set to the minimum flow rate.

2. The method of claim 1, wherein the relationship is a ratio and identifying the relationship comprises computing the ratio between the closed system rate of pressurization and the minimum flow rate.

3. The method of claim 2, wherein limiting the closed system rate of pressurization comprises:

applying a different flow rate during an operation of the system having a first system volume; and setting the dynamic limit based on the ratio and the different flow rate, the dynamic limit being set independent of the first system volume.

4. The method of claim 3, wherein the ratio is used to set the dynamic limit for each possible system volume.

5. The method of claim 2, wherein the system computes the ratio without knowing a configuration of the system and the system volume of the configuration.

6. The method of claim 1, wherein the solvent comprises carbon dioxide.

7. The method of claim 1, wherein the rate of pressurization is restricted by a valve assembly in a pressure regulator that is controlled by an actuator control signal.

* * * * *